(12) United States Patent
Siman (10) Patent No.: US 12,422,433 B2
(45) Date of Patent: *Sep. 23, 2025

(54) BLOOD BIOMARKER THAT PREDICTS PERSISTENT COGNITIVE DYSFUNCTION AFTER CONCUSSION

(71) Applicant: THE TRUSTEES OF THE UNIVERSITY OF PENNSYLVANIA, Philadelphia, PA (US)

(72) Inventor: Robert Siman, Wilmington, DE (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/447,290

(22) Filed: Aug. 9, 2023

(65) Prior Publication Data

US 2023/0393133 A1 Dec. 7, 2023

Related U.S. Application Data

(62) Division of application No. 14/774,585, filed as application No. PCT/US2014/027716 on Mar. 14, 2014, now Pat. No. 11,761,959.

(60) Provisional application No. 61/792,420, filed on Mar. 15, 2013.

(51) Int. Cl.
   *G01N 33/566* (2006.01)
   *G01N 33/68* (2006.01)

(52) U.S. Cl.
   CPC ....... *G01N 33/566* (2013.01); *G01N 33/6896* (2013.01); *G01N 2333/47* (2013.01); *G01N 2333/4703* (2013.01); *G01N 2800/28* (2013.01); *G01N 2800/2871* (2013.01); *G01N 2800/50* (2013.01); *G01N 2800/52* (2013.01)

(58) Field of Classification Search
   CPC .............. G01N 33/566; G01N 33/6896; G01N 2333/4703; G01N 2800/52
   See application file for complete search history.

(56) References Cited

U.S. PATENT DOCUMENTS

| 9,952,214 B2 | 4/2018 | Siman | |
| 11,761,959 B2 * | 9/2023 | Siman | G01N 33/6896 435/6.12 |
| 12,085,565 B2 * | 9/2024 | Siman | G01N 33/566 |
| 2007/0003982 A1 | 1/2007 | Hayes et al. | |
| 2011/0082203 A1 | 4/2011 | Wang et al. | |
| 2011/0199084 A1 | 8/2011 | Hasan et al. | |
| 2012/0149042 A1 | 6/2012 | Jackowski et al. | |

FOREIGN PATENT DOCUMENTS

WO    WO 2013/020136    2/2013

OTHER PUBLICATIONS

Kay et al., "Definition of mild traumatic brain injury", J Head Trauma Rehabil 1993; 8(3): pp. 86-87.
Ling et al., "Biomarkers of increased diffusion anisotropy in semi-acute mild traumatic brain injury: a longitudinal perspective", Brain, Apr. 2012, vol. 135, No. 4, pp. 1281-1292.
Roberts-Lewis et al., " Immunolocalization of calpain I-mediated spectrin degradation to vulnerable neurons in the ischemic gerbil brain", J Neurosci. Jun. 1994;14(6):3934-44.
Shahim et al., " Blood biomarkers for brain injury in concussed professional ice hockey players", JAMA Neurol. Jun. 2014;71(6):684-92.
Siman et al., "A panel of neuron-enriched proteins as markers for traumatic brain injury in humans", Journal of Neurotrauma, vol. 26, No. 11, Nov. 2009, pp. 1867-1877.
Siman et al., "Biomarker evidence for mild central nervous system injury after surgically-induced circulation arrest", Brain Research, vol. 1213, Jun. 2008, pp. 1-11.
Siman et al., "Evidence that the blood biomarker SNTF predicts brain imaging changes and persistent cognitive dysfunction in mild TBI patients", Frontiers in Neurology, vol. 4, 190, Nov. 2013, pp. 1-8.

* cited by examiner

*Primary Examiner* — Olga N Chernyshev
(74) *Attorney, Agent, or Firm* — Mark S. Cohen; PEARL COHEN ZEDEK LATZER BARATZ LLP (57) ABSTRACT

The invention relates to methods for providing prognosis, diagnosis, and treatment of a mild traumatic brain injury (mTBI) in a computed tomography (CT)-negative subject. The invention further relates to monitoring the severity of brain damage resulting from TBI in a subject and determining the prognosis of a subject that has suffered from mTBI. This invention also relates to methods of predicting who is at risk for developing brain damage and long-term dysfunction.

11 Claims, 1 Drawing Sheet

BLOOD BIOMARKER THAT PREDICTS PERSISTENT COGNITIVE DYSFUNCTION AFTER CONCUSSION

CROSS-REFERENCE TO RELATED APPLICATIONS

This application is a divisional application of Ser. No. 14/774,585, filed Sep. 10, 2015, which is a National Phase application of PCT International Application No. PCT/US14/27716, International filing date Mar. 14, 2014, which claims priority to and the benefit of U.S. Patent Application 61/792,420, filed Mar. 15, 2013, all of which are which is hereby incorporated by reference herein in their entirety.

GOVERNMENT INTEREST

This invention was made with government support under NS056202 awarded by the National Institutes of Health. The government has certain rights in the invention.

FIELD OF INVENTION

The invention relates to methods for providing prognosis, diagnosis, and treatment for a mild traumatic brain injury (mTBI) in a computed tomography (CT)-negative subject. The invention further relates to monitoring the severity of brain damage resulting from mTBI in a subject and determining the prognosis of a subject that has suffered from mTBI. This invention also relates to methods of predicting who is at risk for developing brain damage and long-term dysfunction.

BACKGROUND OF THE INVENTION

Mild traumatic brain injury (mTBI), alternatively referred to as concussion, is the most common neurological injury and affects over 1.5 million children and adults each year in the United States alone, and hundreds of thousands of military personnel worldwide. mTBI is typically undetectable with computed tomography (CT), yet can elicit long-term and clinically significant brain dysfunction in approximately 15-30% of cases. Histopathological and biomechanical findings in experimental animal models and human cases that have come to autopsy suggest that the main underlying structural correlate for long-term functional impairment after mTBI is diffuse axonal injury (DAI), resulting from head rotational acceleration at the moment of injury. Developing neuroradiological methods such as diffusion tensor imaging (DTI) have shown promise for the detection of white matter structural abnormalities after mTBI, but collectively these studies have yielded inconsistent results. Consequently, new approaches are urgently needed for the rapid identification of mTBI patients at risk of developing brain damage and persistent disability.

Blood-based biomarkers for brain damage have long been evaluated as potential prognostic measures in mTBI, but none has emerged thus far as a means of identifying at an early and potentially treatable stage those cases of mTBI with evolving brain damage leading to long-term dysfunction. For example, a number of proteins expressed predominantly in the nervous system become detectable in the blood during the acute post-injury period in some mTBI cases, including the astrocyte-enriched proteins S100β and glial fibrillary acidic protein (GFAP), along with the neuron-enriched neuron-specific enolase (NSE), ubiquitin C-terminal hydrolase L1 (UCH-L1), and a proteolytic fragment of tau.

Blood levels of these markers for brain damage are reportedly elevated following injuries categorized as mild based on clinical examinations using the Glasgow Coma Scale. However, these studies have focused predominantly on TBI cases that also show head CT abnormalities, and based on the positive CT findings these patients would be diagnosed with moderate TBI or "complicated" mTBI at most centers. Positive CT findings are known to be associated with poorer long-term outcomes after TBI, and the presence of intracranial hemorrhages suggests that the blood-brain barrier exhibits at least transient permeability that could impact blood-based biomarker measures. Unfortunately, for the much more common instances of CT-negative mTBI, blood-based markers for brain injury have yet to be discovered that are strong predictors of structural damage and long-term functional outcome.

Therefore, there is a need in the art for neurodegeneration biomarkers released from degenerating neurons that are indicative of CT-negative mTBI. The present invention addresses this need by providing a method for using calpain-cleaved αII-spectrin N-terminal fragment (SNTF) as a mechanism-based marker for the calpain-associated necrotic mode of neurodegeneration following mTBI.

SUMMARY OF THE INVENTION

In one embodiment, the invention relates to a method of providing a prognosis for a subject having suffered from a computed tomography (CT)-negative mild traumatic brain injury (mTBI), said method comprising: obtaining a biological sample from said subject; analyzing said sample to determine the level of a biomarker associated with the presence of mTBI, and comparing said level of said biomarker to the level of a pre-determined standard, wherein said biomarker is a calpain-cleaved αII-spectrin N-terminal fragment (SNTF), thereby providing a prognosis for subject having suffered from mTBI.

In another embodiment, the invention relates to a method of monitoring response to therapy in a subject having suffered from a computed tomography (CT)-negative mild traumatic brain injury (mTBI), said method comprising: obtaining a biological sample from said subject receiving said therapy; analyzing said sample to determine the level of a biomarker associated with the presence of mTBI, and comparing said level of said biomarker to the level of a pre-determined standard, thereby monitoring a response to therapy in a subject having suffered from mTBI.

In another embodiment, the invention relates to a method for identifying a subject at risk of suffering from a mild traumatic brain injury (mTBI)-associated abnormality in white matter structure or a long-term dysfunction, said method comprising: obtaining a biological sample from said subject; analyzing said sample to determine the level of a biomarker associated with the presence of mTBI, and comparing said level of said biomarker to the level of a pre-determined standard, wherein said biomarker is a calpain-cleaved αII-spectrin N-terminal fragment (SNTF), thereby identifying a subject at risk of suffering from a mild traumatic brain injury (mTBI)-associated abnormality in white matter structure or a long-term dysfunction.

In another embodiment, the invention relates to a method for diagnosing a mild traumatic brain injury (mTBI) in a subject having a negative computed tomography (CT) test result, said method comprising: obtaining a biological sample from said subject; analyzing said sample to determine the level of a biomarker associated with the presence of said mTBI, and comparing said level of said biomarker to the level of a pre-determined standard, thereby diagnosing mTBI.

In another embodiment, the invention relates to a method for treating a mild traumatic brain injury (mTBI) in a subject having a negative computed tomography (CT) test result, said method comprising: obtaining a biological sample from said subject; analyzing said sample to determine the level of a biomarker associated with the presence of said mTBI, comparing said level of said biomarker to the level of a pre-determined standard, thereby prognosing or diagnosing mTBI, and treating said subject based on the prognosis or diagnosis of said mTBI.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

In one aspect, provided herein is a method for providing prognosis, diagnosis, or treatment for a mild traumatic brain injury (mTBI) in a subject having a negative computed tomography (CT) test result, said method comprising: obtaining a biological sample from said subject; analyzing said sample to determine the level of a biomarker associated with the presence of said mTBI, and comparing said level of said biomarker to the level of a pre-determined standard, thereby providing prognosis, diagnosis, or treatment for said mTBI. In one embodiment, the biomarker obtained from the biological sample according to the methods provided herein is correlated to brain damage and long-term functional disability.

In one embodiment, the standard is determined by measuring the level of said biomarker in a subject or pool of subjects having sustained an orthopedic injury or in a normal uninjured subject or pool of subjects. In another embodiment, the standard is taken from a subject or pool of subjects correctly diagnosed as being normal or healthy.

In one embodiment, diagnosing a mTBI further permits assessing a risk of said mTBI evolving to brain damage and leading to long-term dysfunction. In another embodiment, assessment of a risk of said mTBI evolving to long-term dysfunction permits therapeutic intervention at an early stage.

In one embodiment, the type of brain damage associated with mTBI is a white matter structural abnormality. In another embodiment, the white matter structural abnormality or damage is in the corpus callosum region. In another embodiment, the abnormality or damage is in the uncinate fasciculus. In another embodiment, the abnormality or damage is in the right brain frontal lobe. In another embodiment, the abnormality or damage is in the left frontal lobe. In another embodiment, the abnormality or damage is diffuse axonal injury (DAI).

Brain damage can be assessed by neuroimaging techniques and long-term congnitive assessment. In one embodiment, the present invention provides for a combined assessment of brain damage comprising assessing a biomarker level (or panel of biomarkers) in a biological sample obtained from a subject having suffered a mTBI, by using diffusion tensor imaging (DTI), and by using neuropsychological/behavioral methods. Diffusion tensor imaging (DTI) is well known in the art and it is used to measure the fractional anisotropy (FA) and the apparent diffusion coefficient (ADC) in a biological tissue.

In one embodiment, a concussion is a mTBI. In another embodiment, mTBI is caused by a head injury, where the head injury is, in another embodiment, blunt trauma, acceleration, or deceleration forces. It will be appreciated that such head injuries can be characterized by having one or more of the following conditions: (1) observed or self-reported contusion, disorientation, or impaired consciousness, dysfunction of memory at the time of the injury, loss of consciousness lasting less than 30 minutes; and, (2) symptoms such as headache, dizziness, fatigue, irritability, and poor concentration soon after the injury. Head injuries are also categorized as mild based on clinical examinations using the Glasgow Coma Scale. In one embodiment, the head injury has a Glasgow Coma Scale score of 13-15 upon examination at an emergency center, with no abnormal findings on head CT, duration of loss of consciousness for no more than 30 minutes, post-traumatic amnesia for less than 24 hours, and an Abbreviated Injury Score (AIS) S3 and an ISS of <12 modified to exclude the head region.

In one embodiment, the level of the biomarker in a biological sample obtained from a subject, as provided herein, is independently associated with mTBI and clinically important parameters in mTBI. In another embodiment, the biomarker is indicative of the severity of said subject's condition. In another embodiment, comparing said level of said biomarker in said biological sample to said level of said standard permits diagnosing the severity of mTBI. In another embodiment, sustained levels of said biomarker are associated with a subsequent increased risk of long-term neurological dysfunction.

In one embodiment, a biological sample is blood, sera, plasma, cerebro spinal fluid (CNS), DNA, tissue biopsy, organ biopsy or their combination.

In one aspect, provided herein is a method of monitoring response to therapy in a subject having suffered from a computed tomography (CT)-negative mild traumatic brain injury (mTBI), said method comprising: obtaining a biological sample from said subject receiving said therapy; analyzing said sample to determine the level of a biomarker associated with the presence of mTBI, and comparing said level of said biomarker to the level of a pre-determined standard, thereby monitoring a response to therapy in a subject having suffered from mTBI.

In one embodiment, the biomarker in said biological sample is correlated to brain damage and long-term functional disability. In another embodiment, monitoring response to a therapy further permits optimally adjusting said therapy to reduce a risk of said mTBI evolving to brain damage leading to long-term dysfunction. In another embodiment, comparing a level of the biomarker or a panel of biomarkers in said biological sample to said level of said standard or a pool of standards permits monitoring the response of said therapy. In another embodiment, wherein decreasing levels of said biomarker as a result of said therapy are associated with a subsequent decreased risk of long-term neurological dysfunction.

In one aspect, provided herein is a method of providing a prognosis for a subject having suffered from a computed tomography (CT)-negative mild tramatic brain injury (mTBI), said method comprising: obtaining a biological sample from said subject; analyzing said sample to determine the level of a biomarker associated with the presence of mTBI, and comparing said level of said biomarker to the level of a pre-determined standard, wherein said biomarker is calpain-cleaved αII-spectrin N-terminal fragment (SNTF), thereby providing a prognosis for subject having suffered from mTBI.

In one aspect, provided herein is a method for identifying a subject at risk of suffering from a mild traumatic brain injury (mTBI)-associated abnormality in white matter structure or a long-term dysfunction, said method comprising: obtaining a biological sample from said subject; analyzing said sample to determine the level of a biomarker associated with the presence of mTBI, and comparing said level of said biomarker to the level of a pre-determined standard, wherein said biomarker is a calpain-cleaved αII-spectrin N-terminal fragment (SNTF), thereby identifying a subject at risk of suffering from a mild traumatic brain injury (mTBI)-associated abnormality in white matter structure or a long-term dysfunction.

In one embodiment, the standard is determined by measuring the level of said biomarker or a pool of biomarkers in a subject having sustained an orthopedic injury or in a normal uninjured subject. In another embodiment, wherein comparing the level of biomarker or pool of biomarkers in said biological sample to said level of said standard or pool of standards permits identifying a subject at risk of suffering from a mild traumatic brain injury (mTBI)-associated abnormality in white matter structure or a long-term dysfunction.

In one embodiment, the biomarker provided herein is a calpain-cleaved αII-spectrin N-terminal fragment (SNTF). In one embodiment, SNTF is a marker for mTBI and its blood levels are related to white matter abnormalities and long-term functional disability. In another embodiment, detecting the presence of SNTF in a biological sample obtained from a subject shortly after mTBI is indicative of a risk of developing white matter tract structural damage and long-term disability.

The present invention demonstrates that the blood level of the neurodegeneration biomarker SNTF identifies patients with mTBI likely to have both white matter changes with advanced neuroimaging suggestive of DAI, and also cognitive dysfunction that persists for at least 3 months (see Examples herein).

In some embodiments, the injury-induced elevation in plasma SNTF in mTBI cases triggers calpain activation and spectrin degradation within vulnerable axons, followed by efflux of the protein fragment into the brain parenchyma and bloodstream in association with the axon tract damage underlying brain functional impairment.

In one embodiment, detecting the presence of neurodegeneration markers in a biological sample obtained from a subject shortly after mTBI is indicative of a risk of developing white matter tract structural damage and long-term disability. In another embodiment, detecting the presence of neurodegeneration markers in a biological sample obtained from a CT-negative subject shortly after mTBI is indicative of a risk of developing white matter tract structural damage and long-term disability.

In one embodiment the invention further encompasses functional variants of the SNTF. In another embodiment, the biomarker is the N-terminal fragment of α-spectrin. α-spectrin (alpha chain of spectrin) is a protein that in humans is encoded by the SPTA1 gene. Spectrin is an actin crosslinking and molecular scaffold protein that links the plasma membrane to the actin cytoskeleton, and functions in the determination of cell shape, arrangement of transmembrane proteins, and organization of organelles. It is a tetramer made up of alpha-beta dimers linked in a head-to-head arrangement. This gene is one member of a family of alpha-spectrin genes. The encoded protein is primarily composed of 22 spectrin repeats which are involved in dimer formation. It forms weaker tetramer interactions than non-erythrocytic alpha spectrin, which may increase the plasma membrane elasticity and deformability of red blood cells. Mutations in this gene result in a variety of hereditary red blood cell disorders, including elliptocytosis type 2, pyropoikilocytosis, and spherocytic hemolytic anemia.

In one embodiment, the level of the biomarker provided herein is elevated in a biological sample obtained from a patient having suffered mTBI. In another embodiment, the biomarker is expressed in a biological sample obtained from a subject having suffered from mTBI.

In another embodiment, provided herein are methods for analyzing nucleic acid expression of the biomarkers provided herein. It will be appreciated that the term "nucleic acid" can encompass phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules").

In another embodiment, the invention encompasses use of SNTF as a single or panel of biomarkers for potential clinical diagnosis, risk assessment or prognosis. In another embodiment, this would lead to improved risk stratification and the use of directed therapy to modify known factors that are associated with worse outcomes.

In another embodiment, the methods provided herein further comprise jointly using first a SNTF biomarker and an additional neurodegenerative biomarker. In another embodiment, the association of SNFT with adverse outcomes is independent of the additional biomarker. In another embodiment, the assessment of the biomarkers jointly improves risk assessment over either marker alone in subjects with mTBI.

In another embodiment, mTBI leads to acute brain damage and long-term dysfunction. In another embodiment, the long-term dysfunction is a sensory disfunction. In another embodiment, the dysfunction is a motor dysfunction.

In one embodiment, the subject is a human subject. In another embodiment, the subject is being monitored for brain damage. In another embodiment, the subject is undergoing therapy for brain damage.

The term "standard" encompasses pooled samples from healthy subjects. In another embodiment, the standard may be ethnically- or gender- or age-matched recipients. It is to be understood that the standard may be derived from any subject, or pool of subjects, whose biomarker level profile is sufficient to detect even minute relative differences in biomarker levels, when compared to a test sample, or in another embodiment, to a subject that has mTBI with evolving brain damage leading to long-term dysfunction. In another embodiment, a standard is determined as such by a skilled artisan.

In another embodiment, the standard is the average biomarker level of at least one biomarker in a biological sample of the invention taken from a pool of subjects. In another embodiment, the standard is the mean biomarker level profile taken from a pool of subjects.

In another embodiment, the standard is the median biomarker level in a biological sample taken from a pool of subjects. In another embodiment, the standard is the median biomarker level of one biomarker of the invention taken from a pool of subjects. In another embodiment, the standard is the median biomarker level of at least one or more biomarkers of the invention taken from a pool of subjects.

In another embodiment, the method involves the detection of level of said biomarker in a biological sample. In another embodiment, the level in of the biomarker in a biological sample obtained from a subject as provided herein, is indicative of the severity of the subject's condition. In yet another embodiment, the biomarker level is elevated relative to the level of a standard. In yet another embodiment, comparing the biomarker level in a biological sample of a standard permits measuring the severity of brain damage in a subject. In another embodiment, it permits diagnosing the severity of brain damage in the subject. In another embodiment, it permits monitoring the severity brain damage in the subject. In another embodiment, it permits determining the prognosis of brain damage in the subject. In another embodiment, it permits monitoring the therapeutic response of a subject following mTBI. In another embodiment, it permits monitoring said subject for long-term dysfunction.

In another embodiment the biomarker is present in blood, sera, plasma, saliva, sperm, urine, mucous, cerebral spinal fluid, or any combination thereof and such presence is independently associated mTBI. In another embodiment a biomarker is not present or present in negligible levels in blood, sera, plasma, saliva, sperm, urine, mucous, cerebral spinal fluid, or any combination thereof of a normal subject.

In one embodiment, the level of the biomarker is determined by methods known in the art and include, but are not limited to, PCR, Microarray assays, Immunoblots, notherns, ELISA, fluorescence-based methods (Immunofluorescence, FACS), mass spectrometry, and the like. In another embodiment, any other method known in the art is used for measuring/analyzing/quantifying the level of a biomarker provided herein.

As used herein, the term "expression" refers to the transcription and stable accumulation of sense (mRNA) or antisense RNA derived from a nucleic acid fragment or fragments of the invention. Expression also refers to the translation of mRNA into a polypeptide.

In another embodiment the biomarker/biomarkers expression is/are tissue-specific. In another embodiment, the biomarker/biomarkers expression is/are global. In another embodiment, the biomarker/biomarkers is/are expression is systemic.

In one embodiment, the present invention encompasses several examples of a biological sample. In another embodiment, the biological sample is cells, or in another embodiment tissue or in another embodiment peripheral blood. In one embodiment, the biological sample is obtained from a normal subject. The biological sample may, in one embodiment, be a sample of body fluid. In another embodiment, biological samples refer to, blood, serum, plasma, sperm, urine, mucous, tissue biopsy, organ biopsy, synovial fluid, urine, bile fluid, cerebrospinal fluid, saliva, mucosal secretion, effusion, sweat or their combination.

The proteins of the sample are in one embodiment distributed on various support matrices by methods specific to each matrix. Suitable matrices may, in one embodiment be paper, cellulose acetate, silica, glass, carbon, sugars, plastics and derivatives thereof, and a person skilled in the art will be familiar with the techniques of using such support matrices for the separation of proteins.

"Marker" in the context of the present invention refers to a polypeptide which is differentially present in a sample taken from subjects having a mTBI, as compared to a comparable sample taken from control subjects (e.g., a person with an orthopedic injury or a healthy subject). The term "biomarker" is used interchangeably with the term "marker."

In one embodiment, determining the expression of a biomarker refers to methods to assess mRNA abundance, or in another embodiment, gene product abundance. According to this aspect of the invention, and in one embodiment, gene product refers to the translated protein. In one embodiment, protein abundance reflects gene expression profiles, which may be determined, in other embodiments, by any methods known in the art, such as, but not limited to Western blot analysis, RIA, ELISA, HPLC, functional assays, such as enzymatic assays, as applicable, and others. In one embodiment, expression profile is determined by a change in mRNA levels, or in another embodiment in surface expression, or in another embodiment in secretion or in another embodiment other partitioning of a polypeptide.

As used herein, the term "independently associated" refers to an association that is not necessarily causative, e.g., the level of expression of the biomarker or the presence of the biomarker does not cause the disease or adverse condition provided herein.

As used herein, "increased expression" or "increase in level or "elevated level" refer to an increase in the level of a biomarker relative to the level or activity of the biomarker in a standard. An increase in level may refer to between a 10 to about a 250% increase in biomarker levels in a biological sample. In another embodiment, the increase of the biological maker level taken from a mTBI subject is 1-10%, 11-20%, 21-30%, 31-40%, 41-50%, 51-60%, 61-70%, 71-80%, 81-90%, 91-150% elevated over the levels of a biomarker taken from a normal subject (standard).

As used herein, "compared to a standard", refers to relative changes in biomarker levels where the standard is derived from a single individual, or is derived from pooled subjects who have been successfully categorized as being healthy.

As used herein, the term "measuring" refers to methods which include detecting the presence or absence of marker(s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

As used herein, the phrase "differentially present" refers to differences in the quantity and/or the frequency of a marker present in a sample taken from subjects having mTBI.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the subjects' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

As used herein, the term "diagnostic" refers to identifying the presence or nature of a pathologic condition, for e.g., mTBI. As used herein, the term "sensitivity" of a diagnostic assay refers to the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay may be calculated as 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker can refer to an amount of a marker present in a sample being tested. A test amount can be either in absolute amount (e.g., µg/mL) or a relative amount (e.g., relative intensity of signals).

A "diagnostic amount" of a marker can refer to an amount of a marker in a subject's sample that is consistent with a diagnosis of a brain damage severity or an adverse cardiological condition from an unknown etiology or as a result of mTBI. A diagnostic amount can be either in absolute amount (e.g., 1 µg/mL) or a relative amount (e.g., relative intensity of signals).

A "control amount" or a "standard" amount of a marker can be any amount or a range of amount, which is to be compared against a test amount of a marker. For example, a control amount of a marker can be the amount of a marker in a healthy subject. A control amount can be either in absolute amount (e.g., µg/mL) or a relative amount (e.g., relative intensity of signals).

In another embodiment, the methods provided herein, comprise protein level (amount) measurements. In another embodiment, the methods provided herein, comprise DNA measurements. In another embodiment, the methods provided herein, comprise RNA measurements. In another embodiment, the methods provided herein, comprise mRNA measurements. In another embodiment, methods of measuring the expression level of a given protein used as a biomarker are known to one of average skill in the art. In another embodiment, methods of measuring the transcription level of a given RNA molecule encoding a protein used as a biomarker are known to one of average skill in the art. In another embodiment, methods of measuring the transcription level of a given mRNA molecule encoding a protein used as a biomarker are known to one of average skill in the art.

Methods for capturing, analyzing, quantifying, etc., biomarkers are know in the art, can be captured with capture reagents immobilized to a solid support, such as any biochip described herein, a multiwell microtiter plate or a resin. Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy and radio frequency methods. Using these methods, one or more markers can be detected. MAP analysis represents a highly quantitative and rapid method for simultaneously analyzing a large number of specific antigens using a very small volume of patient plasma. In another embodiment, analysis of circulating antigen levels within a collected biological sample, via MAP, yields results equivalent to an ELISA assay. In another embodiment, MAP yields results with greater efficiency and with a higher throughput capacity, than an ELISA assay.

If desired, the sample can be prepared to enhance detectability of the markers. For example, to increase the detectability of markers, a blood serum sample from the subject can be fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Typically, sample preparation involves fractionation of the sample and collection of fractions determined to contain the biomarkers. Methods of pre-fractionation are well known to those of skill in the art and include, for example, size exclusion chromatography, mass spectrometry, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in PCT/US03/00531, but are not limited to, various kinds of chromatography (e.g., anion exchange chromatography, affinity chromatography, sequential extraction, and high performance liquid chromatography) and mass spectrometry. The separation and detection of the proteins in a plasma sample generates a protein spectra for that sample.

Biomarkers in a sample can also be separated by high-resolution electrophoresis, e.g., one or two-dimensional gel electrophoresis. A fraction containing a marker can be isolated and further analyzed by gas phase ion spectrometry. In another embodiment, two-dimensional gel electrophoresis is used to generate two-dimensional array of spots of biomarkers, including one or more markers. See, e.g., Jungblut and Thiede, Mass Specir. Rev. 16:145-162 (1997).

The two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one-dimensional array are further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures. The pI range of these gels is about 3-10 (wide range gels).

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using a PROTEINCHIP® array) as described herein.

Another method available for use in the present invention is gas chromatography. Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In one embodiment, the biological sample is analysed for the presence of the biomarker(s). In another embodiment, methods for protein analysis that are well known in the arts and are available for use in the present invention include, but are not limited to, Mass Spectrometry, Two-Dimensional Electrophoresis Chromatography High Performance Liquid Chromatography, Reversed-Phase Chromatography Ion Exchange Chromatography, and the like.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

In another embodiment, provided herein is a kit for diagnosing or providing prognosis for a subject developing brain damage as a result of mTBI, comprising equipment including, but not limited to, assays and analytical tools for the assays, both as described herein below in the exemplification, reagents, standards and instructions for analyzing the expression level of two or more biomarkers in a biological sample of the subject.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or PROTEINCHIP® array described above. In one embodiment, the sample is a biological fluid sample taken from a subject. Examples of biological fluid samples include blood, serum, plasma, nipple aspirate, urine, tears, saliva etc. In another embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

When the sample is measured and data is generated, e.g., by methods described herein such as, but not limited to mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" one and determines the closeness of fit between the two signals. The software also can include code indicating which the test sample is closest to, thereby providing a probable diagnosis.

In one embodiment of the present invention, multiple biomarkers are measured. The use of multiple biomarkers increases the predictive value of the test and provides greater utility in diagnosis, categorization of the severity of a subject or patient's condition, patient stratification and patient monitoring. The process called "Pattern recognition" detects the patterns formed by multiple biomarkers and greatly improves the sensitivity and specificity of clinical proteomics for predictive medicine. Subtle variations in data from clinical samples, e.g., obtained using methods provided herein and those know in the art, indicate that certain patterns of protein expression can predict phenotypes such as the presence or absence of a certain disease, a particular stage of a disease, or a positive or adverse response to drug treatments.

As used herein, a protein may have "homology" or be "homologous" to another protein if the two proteins have similar amino acid sequences and have similar biological activities or functions. A protein from two different organisms may have homology or be homologous when the encoded amino acid sequences of the proteins are similar and the proteins have a similar biological activity or function. It is understood that "homologous" does not necessarily imply that there is an evolutionary relationship between the proteins. In one embodiment, a homologous protein exhibits 50% sequence similarity to the wild type protein, or in another embodiment 60% sequence similarity, or in another embodiment 70% sequence similarity. or in another embodiment 80%, 85% or 90% sequence similarity to the wild type protein. or in another embodiment, a homologous protein exhibits 95%, 97%, 98% or 99% sequence similarity.

In one embodiment, the methods of the invention provide for the use of multiple assays, to evaluate differential gene expression. In another embodiment, arrays are used since microarray analysis allows in another embodiment simulataneous gene expression analysis of multiple genes in a high-throughput mode.

In one embodiment, a combination of biomarkers may provide greater predictive value than single markers alone. In another embodiment, the detection of a plurality of markers in a sample increases the percentage of true positive and true negative diagnoses and would decrease the percentage of false positive or false negative diagnoses. Thus, the methods of the present invention can include the measurement of more than one biomarker.

In other embodiments, the measurement of markers can involve quantifying the markers to correlate the detection of markers with a probable diagnosis of the mTBI or brain damage, as described herein.

The correlation may take into account the amount of the marker or markers in the sample compared to a control amount of the marker or markers (up or down regulation of the marker or markers) (e.g., in normal healthy subjects). A control can be, e.g., the average or median amount of marker present in comparable samples of healthy subjects. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determining/practicing the methods provided herein.

In another embodiment, a suitable statistical tool, known to one of skill in the art, is used to determine the level of a biomarker relative to a standard.

In one embodiment, continuous measures are described using simple statistics (mean, median, standard deviation, and range) and categorical/ordinal data (e.g. race, gender, and remodeling geometry) with tables and frequencies.

In another embodiment, graphical methods including histograms, scatter plots, and box plots are used to understand aspects of data quality and examine assumptions that underlie parametric and semi-parametric models.

In one embodiment, to better understand the changes in exposure and outcome over time, individual trajectories are plotted as well as group summaries across time, and Kaplan-Meier plots are used to estimate survival probabilities.

In one embodiment the methods provided herein further comprise managing subject treatment based on the status. Such management describes the actions of the physician or clinician subsequent to determining the severity of brain damage. For example, if the result of the methods of the present invention is inconclusive or there is reason that confirmation of status is necessary, the physician may order more tests. Alternatively, if the status indicates that treatment is appropriate, the physician may schedule the patient for treatment. Likewise, if the result is negative, e.g., the status indicates no need for brain damage treatment is needed, no further action may be warranted. Furthermore, if the results show that treatment has been successful, no further management may be necessary. The invention also provides for such methods where the biomarkers (or specific combination of biomarkers) are measured again after subject management. In these cases, the methods are used to monitor the status of the severity of brain damage in a subject. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

In yet another embodiment, the markers are used in heredity studies to determine if the subject is at risk for developing a more severe case of brain damage.

"Solid support" refers to a solid material which can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed. "Monitoring" refers to recording changes in a continuously varying parameter.

In one embodiment, provided herein is a kit comprising reagents for detecting the biomarker levels, wherein the reagents may include antibodies, nucleic acids, which may hybridize to mRNA isolated from a biological sample, and the like. In one embodiment, reagents may be labelled, or in another embodiment nucleic acids isolated from a biological sample are labelled. In another embodiment, the kit provides instructions for detecting the label qualitatively in another embodiment, quantitatively.

In another embodiment the kit further comprises a buffering agent, or in another embodiment, a preservative, or in another embodiment a protein stabilizing agent. In one embodiment, the kit further comprises an enzyme or a substrate. In one embodiment, the substrate may be a means of detecting a label, or in another embodiment the expressed protein product itself. In one embodiment, the kit further comprises reagents that are necessary for detection of nucleic acids, amino acids or hybridization signals for nucleic acids.

In one embodiment, detecting differential expression of the genes via the kits of the invention is accomplished using established PCR, ELISA, RIA, and other similarly recognized methods, and the reagents comprise those appropriate for the particular assay for detection.

In one embodiment, the results obtained are compared to a standard, which, in another embodiment, may comprise a series of standards, which, in another embodiment is used in the kits of the invention for quantification of differential levels of the biomarker or differential expression. In one embodiment, the standard may comprise any embodiment listed herein, and in another embodiment, will be suitable for a particular application of the kit. In one embodiment, the standard comprises antibodies for detecting a standard biomarker. In one embodiment, the standard comprises nucleic acids when the kit is used for the determination of nucleic acid profile, or in another embodiment the standard is a protein when the kit is used for the determination of expressed protein profile.

In one embodiment, the kit may be adapted for high-throughput screening, and comprise a microarray.

In one embodiment, the kit further comprise agents, which in another embodiment may comprise antibodies, or other agents which detect activity or in another embodiment expression of the translated protein product. In one embodiment the agents comprise antibodies that detect the presence of specific nucleic acids.

In one embodiment, the kit comprises a microarray, which comprises cRNA of the genes indicated, and others. In one embodiment, the kit may comprise standard oligonucleotide probes, PCR reagents and detectable labels. In another embodiment, the kit may comprise biological samples taken from human subjects. The standard will comprise all embodiments listed herein for the standard, including in one embodiment nucleic acid from pooled samples as provided herein.

In one embodiment, the kit further comprises a positive and negative control, wherein said standards can be assayed and compared to the test sample.

In one embodiment, the kit may further comprise labeled cDNA. Fluorescently labeled cDNA probes may be generated through incorporation of fluorescent nucleotides by reverse transcription of RNA extracted from samples of interest Such methods have been shown to have the sensitivity required to detect rare transcripts, which are expressed at a few copies per cell, and to reproducibly detect at least approximately two-fold differences in the expression.

In one embodiment, the methods of this invention employ probes and primers, which may include repetitive stretches of adenine nucleotides (poly-A tails) normally attached at the ends of the RNA, for the identification of differentially expressed genes. In another embodiment, kits of this invention may comprise such probes.

In one embodiment, the biomarker is a functional biomarker or a functional fragment thereof. In another embodiment, the biomarker is a functional variant or fragment thereof of a biomarker provided herein. In another embodiment the biomarker is a homolog of a biomarker provided herein, where in another embodiment, it is a paralog or an ortholog of a biomarker provided herein.

In one embodiment, cRNA refers to complementary ribonucleic acid or substantially complementary ribonucleic acid. In another embodiment, cRNA refers to the hybridization or base pairing between nucleotides or nucleic acids, such as, for instance, between the two strands RNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair in one embodiment, with at least about 70% of the nucleotides of the other strand, or in another embodiment with about 90% to 95%, and in another embodiment with about 98 to 100%. The invention also provides a method for treating a mild traumatic brain injury (mTBI) in a subject having a negative computed tomography (CT) test result. The method includes the prognosis or diagnosis of said mTBI of the invention and, based on the prognosis or diagnosis, treating said mTBI in said subject.

As used herein, the term "treating" may encompass curing, preventing, reducing the incidence of, ameliorating symptoms of, to inducing remission of, or slowing the progression of a disease. The terms "reducing", "suppressing" and "inhibiting" refer to lessening or decreasing.

The term "about" as used herein means in quantitative terms plus or minus 5%, or in another embodiment plus or minus 10%, or in another embodiment plus or minus 15%, or in another embodiment plus or minus 20%.

The term "subject" refers to a mammal, including a human, in need of therapy for, or susceptible to, a condition or its sequelae. The term "subject" does not exclude an individual that is normal in all respects. The term "patient" is encompassed by the term "subject".

The following examples are presented in order to more fully illustrate the preferred embodiments of the invention. They should in no way be construed, however, as limiting the broad scope of the invention.

EXAMPLES

Materials and Methods

Study Participants.

The Institutional Review Boards of the University of Pennsylvania and Texas Medical Center, Houston, reviewed and approved the study. All participants in this study provided written informed consent (or assent if written consent was given by the minor's parent) and were recruited and assessed with approval from and according to the ethical guidelines of the Institutional Review Boards of the recruiting institutions. All procedures were conducted in accord with the ethical standards of the Helsinki Declaration of 1975, as revised in 2000.

This neurodegeneration biomarker study examined 38 participants with plasma collected within 24 hours of injury. Of those, 17 sustained a mTBI, 13 sustained an orthopedic injury (OI) and 8 were uninjured controls (UC). This effort was part of a larger study (n=205) comprising right-handed participants of ages 12-30 years, who were recruited and tested on neuropsychological and brain imaging measures at baseline (within 96 hours of injury), and at follow-up sessions at 1 month (neuropsychological measures only) and 3 months. Participant recruitment was from an unselected series of patients admitted to emergency centers in the Texas Medical Center, Houston, including Ben Taub General Hospital, Texas Children's Hospital, and Memorial Herman Hospital, or, for the uninjured control group, from the greater Houston metropolitan area. The smaller biomarker study group did not differ significantly from the larger study sample on age, socioeconomic status (SES), race, gender, or extracranial Injury Severity Score (ISS).

The 17 participants providing plasma samples with mTBI, as defined by criteria from the Centers for Disease Control, had an injury to the head from blunt trauma, acceleration, or deceleration forces with one or more of the following conditions: (1) observed or self-reported contusion, disorientation, or impaired consciousness, dysfunction of memory at the time of the injury, loss of consciousness lasting less than 30 minutes; and (2) symptoms such as headache, dizziness, fatigue, irritability, and poor concentration soon after the injury. Additional inclusion criteria were a Glasgow Coma Scale score of 13-15 upon examination at an emergency center, no abnormal findings on head CT, duration of loss of consciousness for no more than 30 minutes, post-traumatic amnesia for less than 24 hours, and an Abbreviated Injury Score (AIS)≤3 and an ISS of <12 modified to exclude the head region. Comparator participants were of two cohorts. For one, participants with OI were recruited less than 96 hours post-injury provided they met the following criteria: right-handed, 12-30 years old, no loss of consciousness, no post-traumatic amnesia, no overt intracranial injury, AIS<3 for any region of the body and an ISS 12, and a normal brain CT (if done). A second UC cohort consisted of 8 healthy participants who had not sustained any injury, but were similar to the two injury groups in age, gender and level of education.

Exclusions included non-fluency in either English or -Spanish, failure to provide adequate contact information for scheduling follow-up assessments, blood alcohol level>200 mg/dL, previous hospitalization for head injury, pregnancy when screened prior to brain imaging, pre-existing neurologic disorder associated with cerebral dysfunction and/or cognitive deficit (e.g., cerebral palsy, mental retardation, epilepsy) or diagnosed dyslexia, pre-existing severe psychiatric disorder (e.g., bipolar disorder, schizophrenia), and contraindications to undergoing MRI. The OI comparison group was included to control for risk factors that predispose to injury, including preexisting behavioral problems, learning disabilities, and family variables, along with a general trauma context similar to those with mTBI. The uninjured group was included to examine effects not due to injury and to compare injured patients to the general young adult population. All participants provided written informed consent (or assent if written consent was given by the minor's parent) and were recruited and assessed with approval from and according to the ethical guidelines of the recruiting institutions.

Neurobehavioral Assessments.

Participants were administered tests of cognition and assessed for symptoms related to post-concussive injury. For comparison with neurodegeneration biomarker findings, we analyzed data from three domains, speed of processing, executive memory and cognitive flexibility, along with symptoms of concussion. The analyses were conducted by investigators blinded to the plasma biomarker data.

Rivermead Post Concussion Symptoms Questionnaire (RPCS).

The RPCS is a 16-item self-report of cognitive, emotional, and somatic complaints that are commonly reported following mTBI. Factor analyses have elicited a 3-factor solution comprising cognitive, somatic, and emotional problems, although different factor structures have been reported. The participants were asked to rate the severity of each symptom (currently compared to pre-injury levels) from 0—'not experienced at all' to 4—'severe problem.' The primary variable was the total score.

Symbol-Digit Modalities Test (SDMT).

This is a timed substitution task with written and oral response modalities and is highly sensitive to processing speed deficits in the 8-78 year age range. Using a reference key, each examinee was asked to pair specific numbers with given geometric symbols within 90 seconds. The number of correct responses in the written modality was the variable used in this study.

KeepTrack Task (KT).

This updating task requires adding and deleting items in working memory according to semantic category, and the maintenance of semantic categorical representations. It has been validated in the mild TBI population. The variable used was the mean percent correct items per list recalled.

Diffusion Tensor Imaging.

All participants underwent MRI without sedation on a Philips 3.0 Tesla Achieva scanner. Rigorous quality assurance testing was performed including American College of Radiology phantom testing: no concerns with quality assurance were noted during the course of the study.

An axial single-shot spin-echo echo-planar imaging sequence with 30 diffusion-encoding directions was used for DTI acquisition. Other parameters included a 256 mm field of view, an acquisition voxel size of 2×2×2 $mm^3$, repetition time of 11526 ms, echo time of 51 ms, sensitivity encoding (SENSE) reduction factor of 2, two B factors (0 $s/mm^2$ low B, and 1000 s/mm high B), with two acquisitions to average the signal of the two DTI scans in order to ensure better signal-to-noise ratio. DTI acquisition consisted of 70 slices. A SENSE 8-channel head coil was used.

Image Processing

The corpus callosum, right and left uncinate fasciculi, and right and left frontal lobes were selected as structures of interest due to their known vulnerability in DTI studies of TBI and their presumed relation to the measures of speed of cognitive processing, memory updating, and executive function, and post-concussion symptoms. Additionally, DTI measurement of these structures has been shown to be reproducible both between and within raters on quantitative tractography using previously published protocols. In this study, DTI data were analyzed twice by a single rater to establish intra-rater reliability using intra-class correlational coefficients (ICCs). A subset of the images was analyzed by two raters to establish inter-rater reliability. ICCs for all measurements were above 0.95.

Quantifying the Neurode Generation Biomarker SNTF

The sandwich immunoassay for quantifying calpain-cleaved αII-spectrin N-terminal fragment (SNTF) from human plasma is a modification of a method published previously, in which the enzymatic amplification and detection steps of ELISA were replaced with electrochemiluminescence detection chemistry. Briefly, 96 well plastic microplates with an underside electrode (Meso Scale Discovery) were coated overnight with the capture antibody, a monoclonal directed at the SH3 domain in the N-terminal portion of the a-spectrin subimit (D8/B7 @ 1/1,000; Abcam). For the antigen capture step, human plasma samples diluted to 40% or SNTF standards (25 μLs/well) prepared in 0.25% bovine serum albumin in Tris-buffered saline (pH 7.4) were added in triplicate for 2 hours at 22° C. The detecting antibody was a purified rabbit IgG prepared in our laboratory reactive with the calpain-generated neoepitope at the carboxyl-end of the calpain-derived a-spectrin ~150 kDa amino-terminal fragment (SNTF; 1/5,000). The specificity of this cleavage site-specific antibody for SNTF has been well established. The reporter probe was goat anti-rabbit IgG conjugated to ruthenium (Sulfotag, Meso Scale Discovery, Rockville, MD; 1/500). In the presence of read buffer containing tripropylamine and application of current to the plate electrode, a chemiluminescent product is produced in proportion to the bound antigen. Chemiluminescent signals were quantified by a SECTOR Imager 2400 system (Meso Scale Discovery). Standard curves were generated using serial dilution of a preparation of a-spectrin partially purified from brain and digested with purified calpain I. Briefly, the digestion was performed for 10 minutes at 30° C. at a 300:1 ratio by weight of spectrin extract:calpain I in a buffer of 5 mM Tris-HCl (pH 7.8), 0.6 M KCl, 5 mM β-mercaptoethanol, 2 mM $CaCl_2$. Purified bovine erythrocyte calpain I for the digest was obtained from Sigma (St. Louis, MO). Reactions were quenched and the calpain I inactivated by addition of 5 mM EDTA followed by freeze-thaw.

One unit of SNTF is defined as the signal derived from the SNTF standard diluted to 1 nanoliter per ml, corresponding to ~500 μg of the spectrin-containing brain extract starting material per ml. The minimum reliable detection sensitivity was 10 units.

Control experiments were performed to distinguish SNTF-related signals from non-specific signals emanating from heterophilic substances that are present in a subset of human plasma samples and confound attempts to measure very small amounts of target antigen.

These control immunoassays were conducted as above, except that the detecting IgG specific for SNTF was replaced with normal IgG purified from pre-immune serum from the same rabbit. SNTF-specific signals were calculated as the difference between the specific and pre-immune detecting IgG signals and converted to standardized units. The immunoassays were conducted and analyzed by investigators blinded to all other patient data.

Results

Example 1: Changes in Long-Term Cognitive Function in a Subset of mTBI Cases

A total of 38 participants provided plasma samples on the day of injury for quantification of the neurodegeneration biomarker SNTF: 17 were diagnosed with mTBI and 13 with orthopedic injury (OI), whereas 8 were uninjured controls (UC). The biomarker study subgroup did not differ from the overall study group in terms of initial injury severity, age, gender, or other factors (Table 1).

Among these cases, brain structural integrity was assessed by DTI within 4 days of injury for 28 of the participants, and brain performance was evaluated by neuropsychological testing within 4 days of injury and at 1 and 3 months thereafter for 27-29 of the participants, depending on the test battery. The three cohorts did not differ significantly from one another in age, gender, or level of education.

In comparison with OI and UC groups, the mTBI group demonstrated overall performance deficits at 3 months post-injury on the Symbol Digit Modalities Test (SDMT), Keep-Track (KT), and Rivermead Post-Concussion Symptoms Questionnaire (RPCS) cognitive, emotional, and somatic subscales, similar to reports from prior studies. Neuropsychological test performance varied widely among the mTBI participants: some performed indistinguishably from the UC group at both early and late time points, while other participants showed impairments at the acute and/or 1 month time point that resolved by 3 months, and a third set exhibited dysfunction persisting out to 3 months.

Example 2: Plasma SNTF is Elevated in a Subset of mTBI Cases

We evaluated SNTF as a candidate plasma biomarker for human mTBI. This α-spectrin fragment is generated by the calpain family of cysteine proteases and accumulates in axons damaged by stretch injury in vitro or TBI in vivo. It is released from neurons upon plasma membrane disruption. SNTF has not been evaluated before as a prognostic marker in mTBI. Here, plasma SNTF measured on the day of injury was above the lower limit of detection of 10 units in an ultrasensitive sandwich immunoassay in a subset of participants: 7 of 17 mTBI cases and 3 of 13 OI cases. In contrast, plasma SNTF was below the lower limit of detection in all 8 UC participants. The immunoassay signals from the positive plasma samples were confirmed as being specific for SNTF, and not from heterophilic substances that can confound human plasma biomarker studies, by control experiments in which the SNTF-specific detecting IgG was replaced with pre-immune IgG isolated from the same rabbit. The SNTF-positive mTBI participants were both male and female and their injuries spanned a variety of mechanisms from sports, assault, motor vehicle/motorcycle crashes, falls, and being struck by a falling object. Among the SNTF positive participants, the plasma sampling time ranged broadly from 1-24 hours post-injury, and the absolute SNTF levels ranged from 20-150 units. The SNTF positive and negative groups did not differ significantly from one another in age or gender.

Example 3: Elevated Plasma SNTF on the Day of Injury is Related to White Matter Damage and Long-Term Cognitive Dysfunction To examine the relationship between plasma SNTF levels on the day of mTBI and DAI, the 28 participants among the mTBI, OI, and UC cohorts with usable neuroradiological data were dichotomized as either SNTF positive or negative, and the two groups were evaluated comparatively for axon tract structural abnormalities by DTI. Compared with the 19 SNTF negative cases analyzed by DTI within 4 days of injury, the 9 SNTF positive cases exhibited significant reductions in FA and increases in ADC in the corpus callosum and uncinate fasciculus (p<05; Table 2). The FA and ADC are thought to quantify the orientation and structural integrity of white matter, and their differences as a function of dichotomized plasma SNTF levels provide evidence that plasma elevations in this neurodegeneration biomarker after injury may be related to DAI.

TABLE 1

Representativeness of biomarker study subgroup relative to participants in the ongoing mTBI study.

|  | Overall Group Mean (+/−S.D.) (n = 205) | Biomarker Group Mean (+/−S.D.) (n = 38) | P-value |
|---|---|---|---|
| Age at Baseline | 20.2 (+/−5.4) | 20.5 (+/−5.8) | 0.80 |
| SES | −0.0028 (+/−0.79) | −0.039 (+/−0.72) | 0.80 |
| Race % non Black | 61 | 60 | 0.87 |
| Gender % Female | 33 | 26 | 0.38 |
| GCS (mTBI) % <15 | 23 | 24 | 0.85 |
| Noncranial Injury Severity | 0.93 (+/−1.17) | 1.37 (+/−1.42) | 0.13 |

There were no differences related to demographics or injury between the biomarker study group and the overall study group (t-test).

TABLE 2

Plasma SNTF is related to diffusion tensor imaging differences in select white matter tracts.

| Region/metric | Mean (SD) All SNTF− (n = 19) | Mean (SD) All SNTF+ (n = 9) | P value | Effect Size |
|---|---|---|---|---|
| Corpus callosum | | | | |
| FA | 0.496 (0.02) | 0.479 (0.01) | 0.034 | 0.91 |
| ADC | 0.821 (0.03) | 0.839 (0.02) | 0.13 | 0.63 |
| Uncinate Fasciculus, Left | | | | |
| FA | 0.405 (0.02) | 0.388 (0.02) | 0.09 | 0.73 |
| ADC | 0.754 (0.03) | 0.775 (0.03) | 0.14 | 0.63 |
| Uncinate Fasciculus, Right | | | | |
| FA | 0.389 (0.01) | 0.367 (0.02) | 0.001 | 1.48 |
| ADC | 0.774 (0.02) | 0.798 (0.03) | 0.035 | 0.89 |
| Frontal Lobes, Left | | | | |
| FA | 0.394 (0.02) | 0.383 (0.02) | 0.26 | 0.47 |
| ADC | 0.765 (0.02) | 0.782 (0.02) | 0.07 | 0.77 |
| Frontal Lobes, Right | | | | |
| FA | 0.382 (0.03) | 0.381 (0.02) | 0.95 | 0.03 |
| ADC | 0.783 (0.02) | 0.794 (0.02) | 0.15 | 0.59 |

Dichotomized plasma SNTF levels on the day of injury discriminate groups on brain white matter structural integrity indexed by diffusion tensor imaging performed within 96 hours. Effect size is reported as Cohen's d, where 0.2-0.49 reflects small, 0.5-0.79 medium, and 0.8 or higher large effect size, and P value is from two-tailed t-test.

Long-term behavioral studies have provided evidence that a subset of CT-negative patients with mTBI develop brain functional disability that can persist for many months post-injury. To examine the prognostic relationship between plasma SNTF levels measured on the day of mTBI and long-term brain function, participants were evaluated within 4 days and again at 1 and 3 months post-injury on a battery of tests for cognitive performance and assessed for post-concussion symptoms. These included the Symbol-Digit Modalities Test (SDMT), which measures speed of cognitive processing and is a sensitive index of cognitive functioning independent of intelligence level, the KeepTrack Task, a measure of memory updating and executive function, and the Rivermead Post-Concussiom Symptoms Questionnaire (RPCS), a self-report assessment of the severity of somatic, emotional and cognitive symptoms after concussion. For groups dichotomized with respect to plasma SNTF levels on the day of injury, there were marked differences in functional measures at both the acute and long-term time points. Plasma SNTF did not discriminate symptomatology on the overall RPCS, but showed an association with impairments in the cognitive and somatic components at 3 months post-injury that did not reach statistical significance. Most importantly, a detectable level of plasma SNTF on the day of injury discriminated test performance at 3 months on the written versions of the SDMT and the KeepTrack task, and the relationship with the former cognitive deficit was highly significant (p<0.01; Table 3).

The significant discrimination in the written and oral versions of the SDMT observed across all study participants based on dichotomized plasma SNTF (Table 3) was even stronger among the mTBI cases by themselves (written SDMT: SNTF+=46.8; SNTF−=59.1; p=0.011; oral SDMT: SNTF+=70.1; SNTF−=53.3; p=0.024).

Figure 1:
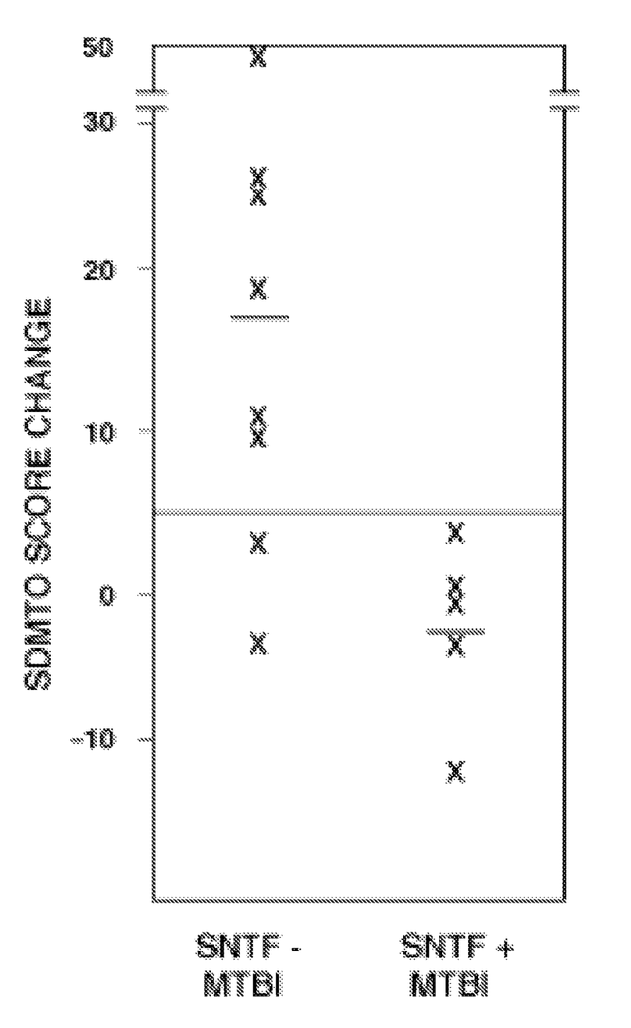
FIG. 1. Plasma SNTF discriminates 3 months changes in cognitive performance after mTBI. The difference in SDMTO scores between the acute (1-4 day) and chronic (3 months) post-injury periods is plotted as a function of dichotomized plasma SNTF levels on the day of mTBI. The difference in cognitive performance recoveries between the biomarker negative and positive Mtbi groups is significant ($p<0.03$, two-tailed t-test).

Plasma SNTF on the day of mTBI also correlated with recovery of cognitive performance. Among the 13 mTBI participants evaluated by the oral SDMT in both the acute (1-4 days) and long-term (3 month) post-injury time periods, test scores for the SNTF—cases improved by 17 points (+/−5.7, s.e.m.), whereas those for the SNTF+ cases worsened by 2.6 points (+/−2.7). The difference in 3 month recovery of cognitive performance as a function of dichotomized plasma SNTF levels was significant (p<0.03). Six of eight SNTF− cases of mTBI showed improvement in cognitive performance over 3 months of 5 points or greater on the oral SDMT, compared with none of the five SNTF+ cases (FIG. 1). Based on this preliminary post-hoc assessment, plasma SNTF on the day of mTBI showed 100% sensitivity and 75% specificity for predicting failure to improve cognitive performance over the first 3 months after a CT-negative mTBI.

TABLE 3

Plasma SNTF on the day of a mTBI relates to impaired cognitive performance at 3 months post-injury.

| Test | All SNTF+ | All SNTF− | Effect size |
|---|---|---|---|
| Symbol-Digit Modalities Test, Written (total correct responses) | 52.00 (12.1) | 63.47 (14.86) | 0.88 (large) |
| KeepTrack Task (Percent correct recalled) | 88.89 (7.8) | 92.72 (5.6) | 0.63 (mod-large) |
| RiverMead Post-Concussion Symptoms (total score) | 9.44 (10.89) | 6.37 (11.08) | 0.28 (small) |

Dichotomized plasma SNTF levels on the day of injury (+/−SD in parentheses) are related to behavioral differences 3 months post-injury. Effect size is reported in Cohen's d, where 0.2-0.49 reflects a small, 0.5-0.79 a medium, and 0.8 or higher a large effect size. The difference in cognitive performance on the written Symbol Digit Modalities Test across all study participants based on plasma SNTF is significant by two-tailed t-test (p<0.04), as is the difference within the mTBI cases by themselves (SNTF+=46.8; SNTF−=59.1; p<0.025).

TABLE 4

Dichotomized plasma SNTF levels on the day of injury correlate with impaired cognitive performance at 3 months.

| Cognitive performance test | Mean (SEM) SNTF negative | Mean (SEM) SNTF positive | P Value |
|---|---|---|---|
| SDMT at 3 months | | | |
| All study subjects | 63.4 (3.4) | 52.0 (4.0) | 0.039 |
| mTBI cases | 59.1 (2.8) | 46.8 (2.9) | 0.011 |
| ΔSDMT over 3 months | | | |
| mTBI cases | +17.5 (5.7) | −2.6 (2.7) | 0.029 |

The SDMT scores were significantly worse for the biomarker positive cases both across all study participants and among the mTBI cases by themselves (two-tailed t-test). In the mTBI group, elevated SNTF on the day of injury also predicted failure to improve cognitive performance over 3 months.

In this study, we provide evidence that the blood level of the neurodegeneration biomarker SNTF identifies mTBI patients on the day of their injury likely to have both white matter changes with advanced neuroimaging suggestive of DAI, and also cognitive dysfunction that persists for at least 3 months.

In contrast to the prior findings with other marker candidates, our results indicate that the blood level of SNTF and potentially other neurodegeneration biomarkers sampled in the acute period after CT-negative mTBI help identify at an early and treatable stage a subset of cases at risk of developing white matter tract structural damage and long-term disability.

The injury-induced elevation in plasma SNTF in a subset of mTBI cases reported here show that functionally impactful mTBI triggers calpain activation and spectrin degradation within vulnerable axons, followed by efflux of the stable fragment SNTF into the brain parenchyma and bloodstream in association with the axon tract damage underlying brain functional impairment.

Increased plasma SNTF post-concussion is related not only to structural evidence for diffuse axonal injury (DAI), but also functional evidence for long-term cognitive impairment. Whereas a subset of the participants with mTBI exhibit no discernible deficits on a battery of cognitive, somatic, or emotional tests post-injury, a second group shows performance deficits that resolve over time, while a third group develops impaired brain performance persisting for at least 3 months post-injury. Strikingly, the dichotomized plasma level of SNTF measured on the day of injury is related to cognitive dysfunction at 3 months, as evidenced by a significant deficit in the SNTF-positive group in the Symbol Digit Modalities Test and trends toward impairments in the KeepTrack test (Table 3) and the cognitive component of the Rivermead Post Concussion Symptoms Questionnaire (RPCS). The ability of plasma SNTF elevations to significantly differentiate long-term cognitive decline holds across all 28 participants in the mTBI, OI, and UC groups and even more strongly among the mTBI cases by themselves. Plasma SNTF on the day of mTBI also discriminated subsequent change in cognitive performance on the Symbol Digit Modalities Test, with a positive SNTF finding predicting failure to improve cognitive performance over 3 months post-injury (FIG. 1).

Overall, the results show that the blood level of SNTF on the day of a CT-negative mTBI can identify a subset of patients at risk of white matter damage and persistent disability. SNTF can have prognostic and diagnostic utilities in the assessment and treatment of mTBI.

Having described the embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for providing a prognosis for and treating a subject having suffered from a computed tomography (CT)-negative mild traumatic brain injury (mTBI), said method comprising:
   obtaining a serum or plasma sample from said subject;
   analyzing said sample to determine the level of a serum or plasma concentration of calpain-cleaved αII-spectrin N-terminal fragment (SNTF);
   comparing said level of said concentration of SNTF to the level of a pre-determined standard;
   providing a prognosis for the subject having suffered from the mTBI based on the level of SNTF in the subject relative to the pre-determined standard, wherein an elevated level of SNTF relative to the pre-determined standard indicates an elevated risk of long-term neurological dysfunction; and
   treating said mTBI in said subject.

2. The method of claim 1, wherein said standard is determined by measuring the level of SNTF in a subject or pool of subjects having sustained an orthopedic injury or in a normal uninjured subject or pool of subjects.

3. The method of claim 1, wherein said mTBI is a concussion, or is caused by a head injury.

4. The method of claim 1, wherein:
the level of said SNTF in said serum or plasma sample is independently associated with mTBI and clinically important parameters in mTBI;
the level of said SNTF is indicative of the severity of said subject's condition;
comparing said level of said SNTF in said serum or plasma sample to said level of said standard permits diagnosing the severity of mTBI;
sustained levels of said SNTF are associated with a subsequent increased risk of long-term neurological dysfunction; or
a combination thereof.

5. A method of treating and monitoring a response to that treatment in a subject having suffered from a computed tomography (CT)-negative mild traumatic brain injury (mTBI), said method comprising:
treating said mTBI in said subject;
obtaining a serum or plasma sample from said subject receiving said treatment;
analyzing said sample to determine the level of a serum or plasma concentration of calpain-cleaved αII-spectrin N-terminal fragment (SNTF);
comparing said level of said SNTF to the level of a pre-determined standard; and
monitoring the response to said treatment by recording changes in the level of said SNTF and/or a difference between the level of the SNTF and the level of the pre-determined standard, and wherein decreasing SNTF levels indicates a subsequent decreased risk of brain damage, long-term functional disability, or long-term neurological dysfunction.

6. The method of claim 5, wherein said standard is determined by measuring the level of SNTF in a subject having sustained an orthopedic injury or in a normal uninjured subject.

7. The method of claim 5, wherein said brain damage is in the right or left frontal lobe.

8. The method of claim 5, wherein said mTBI is a concussion, or wherein said mTBI is caused by a head injury.

9. The method of claim 5, wherein:
the level of said SNTF in said serum or plasma sample is independently associated with mTBI and clinically important parameters in mTBI;
the level of expression of said SNTF is indicative of the severity of said subject's condition;
comparing said level of said SNTF in said serum or plasma sample to said level of said standard permits monitoring the response of said therapy:
decreasing levels of said SNTF as a result of said treatment are associated with a subsequent decreased risk of long term neurological dysfunction; or
a combination thereof.

10. A method for diagnosing and treating a mild traumatic brain injury (mTBI) in a subject associated with a negative computed tomography (CT) test result, said method comprising:
obtaining a biological sample from said subject; analyzing said sample to determine the level of a biomarker associated with the presence of mTBI,
comparing said level of said biomarker to the level of a pre-determined standard, wherein said biomarker is a calpain-cleaved αII-spectrin N-terminal fragment (SNTF)
diagnosing the subject as having suffered from the mTBI based on the level of SNTF in the subject relative to the pre-determined standard, wherein an elevated level of SNTF relative to the pre-determined standard indicates having suffered from the mTBI, and wherein an elevated SNTF level relative to the standard indicates the severity of mTBI, and
treating said mTBI in said subject.

11. The method of claim 10, wherein said standard is determined by measuring the level of said biomarker in a subject having sustained an orthopedic injury or in a normal uninjured subject.

* * * * *